United States Patent
Brewer et al.

(10) Patent No.: US 7,785,270 B2
(45) Date of Patent: Aug. 31, 2010

(54) CATHETER TESTING SYSTEM AND USES THEREOF

(75) Inventors: Robert Brewer, Brookfield, WI (US);
Richard Julius, Waukesha, WI (US);
Michael Julius, Hartland, WI (US);
Joseph Mattano, Nashotah, WI (US);
Kevin Davidson, New Berlin, WI (US)

(73) Assignee: CRS Medical Diagnostics, Inc., Pewaukee, WI (US)

( * ) Notice: Subject to any disclaimer, the term of this patent is extended or adjusted under 35 U.S.C. 154(b) by 595 days.

(21) Appl. No.: 11/713,153

(22) Filed: Mar. 2, 2007

(65) Prior Publication Data

US 2007/0248946 A1    Oct. 25, 2007

Related U.S. Application Data

(60) Provisional application No. 60/778,556, filed on Mar. 2, 2006.

(51) Int. Cl.
*A61B 10/00* (2006.01)
*A61M 5/00* (2006.01)
*A61M 25/00* (2006.01)

(52) U.S. Cl. .................. 600/569; 604/171; 604/264
(58) Field of Classification Search ............... 600/569; 604/171, 264
See application file for complete search history.

(56) References Cited

U.S. PATENT DOCUMENTS

| | | | |
|---|---|---|---|
| 3,861,395 A | | 1/1975 | Taniguchi |
| 4,062,363 A | | 12/1977 | Bonner, Jr. |
| 4,108,162 A | * | 8/1978 | Chikashige et al. .......... 600/569 |
| 4,327,723 A | | 5/1982 | Frankhouser |
| 4,327,735 A | | 5/1982 | Hampson |
| 4,850,957 A | * | 7/1989 | Summers ...................... 604/22 |
| 4,946,440 A | * | 8/1990 | Hall ....................... 604/164.09 |
| 5,020,543 A | | 6/1991 | Rothenberg |
| 5,215,522 A | | 6/1993 | Page |
| 5,370,653 A | * | 12/1994 | Cragg ........................ 606/170 |
| 5,405,755 A | | 4/1995 | Markus |
| 5,407,807 A | | 4/1995 | Markus |
| 5,535,756 A | * | 7/1996 | Parasher ..................... 600/569 |
| 5,702,413 A | * | 12/1997 | Lafontaine .................. 606/159 |
| 5,715,815 A | | 2/1998 | Lorenzen |
| 5,882,332 A | * | 3/1999 | Wijay ......................... 604/508 |
| 5,902,263 A | * | 5/1999 | Patterson et al. .............. 604/22 |
| 6,465,206 B1 | | 10/2002 | Collins |
| 6,588,427 B1 | | 7/2003 | Carlsen |

(Continued)

OTHER PUBLICATIONS

Blackett, R., et al., "A prospective study of subclavian vein catheters used exclusively for the purpose of intravenous feeding" Br. J. Surg., 1978, vol. 65(5), pp. 393-395.

(Continued)

*Primary Examiner*—Max Hindenburg
*Assistant Examiner*—Sean P Dougherty
(74) *Attorney, Agent, or Firm*—Casimir Jones SC

(57) ABSTRACT

The present invention relates generally to devices and systems for detecting infection within catheters. In particular, the present invention provides catheter testing systems configured to sterilely collect a biological sample from the interior of a catheter for purposes of testing the biological sample (e.g., for the presence of fibrin, sepsis, etc.).

21 Claims, 1 Drawing Sheet

U.S. PATENT DOCUMENTS

| | | | |
|---|---|---|---|
| 6,692,504 B2* | 2/2004 | Kurz et al. | 606/127 |
| 6,725,492 B2* | 4/2004 | Moore et al. | 15/104.2 |
| 6,920,662 B2 | 7/2005 | Moore | |
| 7,273,473 B2 | 9/2007 | Owens | |
| 2005/0171493 A1 | 8/2005 | Nicholls | |

OTHER PUBLICATIONS

Bouza, E., et al., "Catheter-related infections: diagnosis and intravascular treatment" Clin. Microbiol. Infect., 2002, vol. 8(5), pp. 265-274.

Cercenado, E., et al., "A conservative procedure for the diagnosis of catheter-related infections" Arch. Intern. Med., 1990, vol. 150(7), pp. 1417-1420.

Dobbins et al., "Endoluminal Brushing in Catheter-Related Sepsis: A 'Sweeping' Statement", 1999 Nutrition, vol. 15 (1) 66-67.

Maki D., et al., "An attachable silver-impregnated cuff for prevention of infection with central venous catheters: a prospective randomized multicenter trial" Am. J. Med., 1988, vol. 85(3), pp. 307-314.

Maki D., et al., "Infection control in intravenous therapy" Ann. Intern. Med., 1973, vol. 79(6), pp. 867-887.

Maki D., et al., "A prospective, randomized trial of gauze and two polyurethane dressings for site care of pulmonary artery catheters: implications for catheter management" Crit. Care Med., 1994, vol. 22(11), pp. 1729-1737.

Maki D., et al., "Prospective randomised trial of povidone-iodine, alcohol, and chlorhexidine for prevention of infection associated with central venous and arterial catheters" Lancet, 1991, vol. 338(8763), pp. 339-343.

Markus S., et al., "Culturing Indwelling Central Venous Catheters in Situ", Infect. Surg., 1989, pp. 157-162.

Mermel L., "The pathogenesis and epidemiology of catheter-related infection with pulmonary artery Swan-Ganz catheters: a prospective study utilizing molecular subtyping" Am. J. Med., 1991, vol. 91(3B), pp. 197S-205S.

Mermel L., "Prevention of intravascular catheter-related infections" Ann. Intern. Med, 2000, vol. 132(5), pp. 391-402.

Moro M., et al., "Risk factors for central venous catheter-related infections in surgical and intensive care units. The Central Venous Catheter-Related Infections Study Group" Infect. Control Hosp. Epidemiol., 1994, vol. 15(4 Pt 1), pp. 253-264.

Richards M., et al., "Nosocomial infections in combined medical-surgical intensive care units in the United States" Infet. Control. Hosp. Epidemiol., 2000, vol. 21(8), pp. 510-515.

Ryan J., "Catheter complications in total parenteral nutrition. A prospective study of 200 consecutive patients" N. Engl. J. Med., 1974, vol. 290(14), pp. 757-761.

Segura M., et al., "Assessment of a new hub design and the semiquantitative catheter culture method using an in vivo experimental model of catheter sepsis" J. Clin. Microbiol., 1990, vol. 28(11), pp. 2551-2554.

Sitges-Serra, A., et al., "Catheter sepsis: the clue is the hub" Surgery, 1985, vol. 97(3), pp. 355-357.

Snydam, D., et al., "Total parenteral nutrition-related infections. Prospective epidemiologic study using semiquantitative methods" Ann. J. Med., 1982, vol. 73(5), pp. 695-699.

Douard, M., et al., "Negative catheter-tip culture and diagnosis of catheter-related bacteremia" Nutrition, 1994, vol. 10(5), pp. 397-404.

Leon, M., et al., Med. Intensiva., 1993, vol. 17, pp. 531-544.

Raad I., et al., "Catheter Related Septicemia: Risk Reduction" Infect. Med., 1996, vol. 13, pp. 807-812, 815-816, 823.

Linares, J., et al., "Diagnosis of catheter-related infection" Rev. Clin. Esp., 1997, vol. 197(Suppl. 2)(1), pp. 19-26.

* cited by examiner

CATHETER TESTING SYSTEM AND USES THEREOF

This application claims priority to U.S. Provisional Application Ser. No. 60/778,556, filed Mar. 2, 2006, herein incorporated by reference in its entirety.

FIELD OF THE INVENTION

The present invention relates generally to devices and systems for detecting infection within catheters. In particular, the present invention provides catheter testing systems configured to sterilely collect a biological sample from the interior of a catheter for purposes of testing the biological sample (e.g., for the presence of fibrin, sepsis, etc.).

BACKGROUND

Central venous catheters are an integral part of modern medical practice and their advantages are beyond doubt. More than 20 million (over 50%) of inpatients in the USA received intravenous therapy every year (see, e.g., Maki D. Pathogenesis, prevention and management of infections due to intravascular devices used for infusion therapy. In: Bisno A, Waldvogel F. eds. Infections associated with indwelling medical devices, 2nd edn. Washington D.C.: American Society for Microbiology, 1994: 155-212; Raad I, et al., Infect Med 1996; 13: 807-812, 815-6, 823; Mermel L A. Ann Intern Med 2000; 132 (5): 391-402; each herein incorporated by reference in their entireties) and almost 5 million required central venous catheterization. However, there are approximately 250,000 catheter-related infections (CRI) and 120,000 episodes of catheter-related bloodstream infection (CR-BSI) annually in the USA (see, e.g., Maki D. Pathogenesis, prevention and management of infections due to intravascular devices used for infusion therapy. In: Bisno A, Waldvogel F. eds. Infections associated with indwelling medical devices, 2nd edn. Washington D.C.: American Society for Microbiology, 1994: 155-212; Raad I, et al., Infect Med 1996; 13: 807-812, 815-6, 823; Mermel L A. Ann Intern Med 2000; 132 (5): 391-402; Maki D, et al., Lancet 1991; 338 (8763): 339-43; each herein incorporated by reference in their entireties).

Data from the NNIS system (US) between January 1992 and February 1998 showed that BSI is the third most frequent nosocomial infection and accounted for 14% of all nosocomial infections (see, e.g., Richards M, et al., Infect Control Hosp Epidemiol 2000; 21 (8): 510-15; herein incorporated by reference in its entirety). BSIs prolong hospital stays from 7 to 21 days and account for an estimated increase in hospital costs of $3,000-40,000 per patient (see, e.g., Jarvis W. Infect Control Hosp Epidemiol 1996; 17 (8): 552-7; Pittet D, et al., JAMA 1994; 271 (20): 1598-601; Haley R, et al., Am J Med 1981 70 (1): 51-8; Arnow P, et al., Clin Infect Dis 1993; 16 (6): 778-84; each herein incorporated by reference in its entirety). In addition, an estimated 10-20% attributable mortality owing to nosocomial CR-BSI has been reported (see, e.g., Jarvis W. Infect Control Hosp Epidemiol 1996; 17 (8): 552-7; herein incorporated by reference in its entirety).

In Europe, and according to the ESGNI-2 point prevalence study, 71% of all patients with BSI had an intravenous line (see, e.g., Bouza E, et al., Clin Microbiol Infect; 5: 2S1-2S12, 1999; herein incorporated by reference in its entirety). BSI accounted for 13% of all nosocomial infections in a Swiss 1-week prevalence study conducted in 1996 and the use of a CVC was an independent risk factor for infection [odds ratio (OR) 3.3] (see, e.g., Pittet D, et al., Infect Control Hosp Epidemiol 1999; 20 (1): 37-42; herein incorporated by reference in its entirety). In different European studies, BSI related to catheter infection accounts for 23.5-66% of all bacteremic episodes (see, e.g., Ronveaux O, et al., Eur J Clin Microbiol Infect Dis 1998; 17 (10): 695-700; Raymond J, et al., Infect Control Hosp Epidemiol 2000; 21 (4): 260-3; Valles J, et al., Clin Infect Dis 1997; 24 (3): 387-95; each herein incorporated by reference in their entireties). The increased cost per survivor in intensive care unit (ICU) patients with a BSI has been estimated at $28,960, with a 25% mortality (see, e.g., Pittet D, et al., JAMA 1994; 271 (20): 1598-601; Pittet D, et al., Arch Intern Med 1995; 155: 1177-84; each herein incorporated by reference in their entireties).

As such, infection within placed catheters is a major problem. The art is in need of improved methods, systems, devices and kits for addressing this problem.

SUMMARY

The present invention relates generally to devices and systems for detecting infection within catheters. In particular, the present invention provides catheter testing systems configured to sterilely collect a biological sample from the interior of a catheter for purposes of testing the biological sample (e.g., for the presence of fibrin, sepsis, etc.).

In certain embodiments, the present invention provides systems and devices for collecting biological sample from the interior of a catheter. In some embodiments, the devices comprise a catheter hub, a sheath, a sheath ring, and a brush. In some embodiments, the catheter hub is hollow and has therein a catheter hub proximal opening and a catheter hub distal opening, wherein the catheter hub distal opening is configured to engage a catheter opening. In some embodiments, the sheath is tubular in shape and has therein an open sheath distal end, a sheath proximal end compartment, and a closed sheath proximal end and an open sheath distal end, wherein the open sheath distal end is securely positioned along the outside of the catheter hub proximal opening. In some embodiments, the sheath ring is hollow and ring shaped, wherein the sheath ring is positioned on the outside of the open sheath distal end and catheter hub proximal end so as to secure the open sheath distal end on the outside of the catheter hub proximal end. In some embodiments, the brush comprises a bristle section, an extended body, and a brush handle, wherein the brush is positioned within the sheath such that the handle is positioned within the sheath proximal end compartment and the bristle section is positioned near the open sheath distal end such that the bristle portion may be advanced or withdrawn through the catheter hub.

The systems and devices are not limited to particular types or kinds of brushes. In some embodiments, the length of the brush is less than the distance of the catheter so as to avoid advancement of the brush beyond the terminus of the catheter. In some embodiments, as the brush is advanced or withdrawn through the catheter hub the brush handle remains positioned within the sheath proximal end compartment, so as to prevent the entire brush from advancing beyond the sheath.

The systems and devices are not limited to particular types or kinds of catheter hubs. In some embodiments, the catheter hub is a slip luer.

The systems and devices are not limited to a particular positioning of the sheath and catheter hub. In some embodiments, the positioning of the sheath distal end and the catheter hub proximal end with the sheath ring results preserves a sterile field within the sheath and the catheter hub.

In some embodiments, the bristle section of the brush is designed to collect biological sample from the interior of a catheter. In some embodiments, the bristles are of uniform length. In some embodiments, the bristles have varied length. In some embodiments, the material of the sheath is 1 ml polyethylene.

In certain embodiments, the present invention provides methods for collecting a biological sample from the interior of a catheter, comprising providing a subject having a catheter and a catheter testing system and/or device of the present invention, attaching the catheter hub distal end onto the catheter, advancing the brush through the catheter hub and into the catheter such that the brush does not advance beyond the terminus of the catheter, collecting a biological sample from the interior of the catheter with the bristle portion of the brush, and withdrawing the brush from the catheter and into the sheath. In some embodiments, the advancing, collecting and withdrawing is completed within a sterile field. In some embodiments, the collected biological sample is tested for infection.

In certain embodiments, the present invention provides a kit for collecting a biological sample from the interior of a catheter, comprising a catheter testing system and/or device of the present invention. In some embodiments, the kits further comprise one or more additional agents including, but not limited to, an instruction sheet, medical gloves, a catheter, a facemask, alcohol swabsticks, vacutainer tubes, an overwrap drape, a medical procedure drape, and a specimen transport bag.

DETAILED DESCRIPTION

Figure 1:
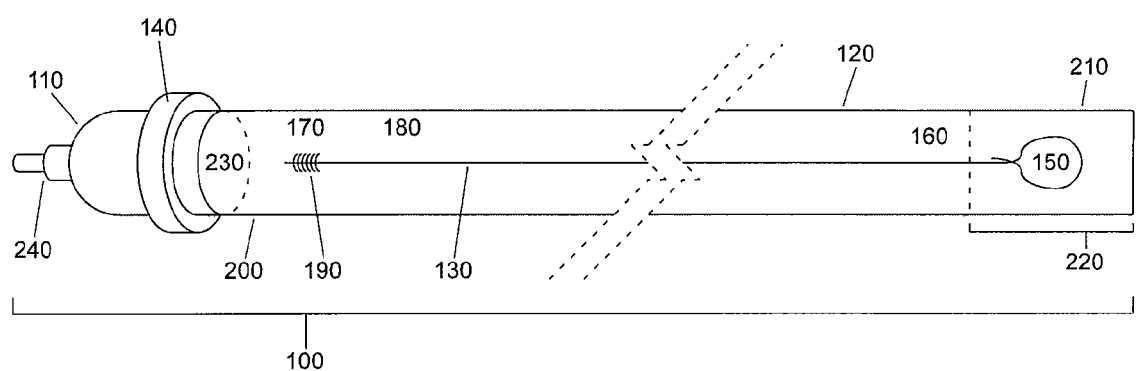
FIG. 1 shows a catheter testing system embodiment.

Infection related to catheter placement may develop by, for example, five major mechanisms, of which the external surface pathway is the most important source of infection (see, e.g., Maki D, et al., Ann Intern Med 1973; 79 (6): 867-87; Snydman D, et al., Am J Med 1982; 73 (5): 695-9; each herein incorporated by reference in their entireties). These five include: 1) Contamination of the catheter at the time of insertion due to poor aseptic technique; 2) Migration of skin organisms along the catheter external surface; 3) Contamination of the catheter hub from extrinsic or endogenous sources passing through the catheter lumen; 4) Contaminated infusate; and 5) Hematogenous seeding from a distant infection (see, e.g., Bouza, E., et al., Clin. Microbiol. Infect., 2002 8(5):265-274; herein incorporated by reference in its entirety).

For short-term catheters, skin contamination is a most likely mechanism of pathogenesis, whereas for long-term catheters, hub contamination is a frequent cause.

Approximately 65% of CRI originate from the skin flora, 30% from the contaminated hub and 5% from other pathways (see, e.g., Maki D, et al., Crit Care Med 1994; 22 (11): 1729-37; Cercenado E, et al., Arch Intern Med 1990; 150 (7): 1417-20; Maki D, et al., Am J Med 1988; 85 (3): 307-14; Sitges-Serra A, et al., Surgery 1985; 97 (3): 355-7; Segura M, et al., J Clin Microbiol 1990; 28(11): 2551-4; Douard M, et al., Nutrition 1994; 10 (5): 397-404; Moro M, et al., Infect Control Hosp Epidemiol 1994; 15 (4 Pt 1): 253-64; Mermel L, et al., Am J Med 1991; 91 (3B):197S-205S; each herein incorporated by reference in their entireties). This distribution reflects duration of catheterization and type of patient population studied (see, e.g., Widmer A. Intravenous-related infections. In: Wenzel R. ed. Prevention and control of nosocomial infections, 3rd edn. Baltimore, Mass.: Williams & Wilkins, 1997: 771-805; herein incorporated by reference in its entirety).

Inflammatory signs show a poor correlation with CRI, especially in CVC-related infections. Local inflammatory signs at the catheter's portal of entry or tunnel have a highly predictive value for infection but its absence has a very poor negative value. Therefore, microbiological techniques are necessary to identify catheter colonization or infection. Most diagnostic techniques are based on culture of the catheter tip after its removal. However, only about 15-25% of CVC removed because of a suspected infection actually proved to be infected (see, e.g., Ryan J, et al., N Engl J Med 1974; 290 (14): 757-61; Blackett R, et al., Br J Surg 1978; 65 (6):393-5; Leon M, et al., Med Intensiva 1993; 17: 531-44; Linares J, et al., Rev Clin Esp 1997; 197(Suppl 2) (1): 19-26; each herein incorporated by reference in their entireties), and the diagnosis is always retrospective. As such, diagnostic techniques that do not require catheter withdrawal have been developed.

Endoluminal brushes have been used to access the interior of a placed catheter for purposes of collecting biological sample (see, e.g., Markus, S., et al., 1989 Infect. Surg. 157-162; U.S. Pat. No. 5,405,755; U.S. Pat. No. 5,407,807; U.S. Patent Application Publication No. 2005-0171493; each herein incorporated by reference in their entireties). Such approaches, however, are limited due to comprised sterility and undesired advancement of the brush beyond the terminus of the catheter resulting in embolization or subsequent bacteremia (see, e.g., Bouza, E., et al., Clin. Microbiol. Infect., 2002 8(5):265-274; herein incorporated by reference in its entirety).

The catheter testing systems of the present invention overcome the limitations of previous endoluminal approaches. In particular, the catheter testing systems of the present invention utilize endoluminal brushes positioned within a sterilely maintained sheath, and a design configured to prevent the passing of the brush beyond the terminus of the catheter. As such, the catheter testing systems of the present invention improve over previous approaches through reducing the chances for bacteremia and embolization.

Accordingly, the present invention provides systems, devices, kits and methods for collecting a biological sample from the interior of a catheter, and testing said biological sample (e.g., for the presence of fibrin).

In particular, the present invention provide catheter testing systems configured for collecting a biological sample from the interior of a catheter. The present invention is not limited to a particular type or kind of catheter testing system. In some embodiments, as shown in FIG. 1, the catheter testing system 100 comprises a catheter hub 110, a protective sheath 120, a brush 130, and a sheath ring 140. The catheter testing system provides an improvement over existing devices through improved sterility preservation during and after the collecting of a biological sample from the interior of a catheter, and prevention of advancement of the brush beyond the terminus of the catheter (described in more detail below).

Still referring to FIG. 1, the catheter testing systems 100 of the present invention are not limited to a particular type or kind of brush 130 (see, e.g., Markus, S., et al., 1989 Infect. Surg. 157-162; U.S. Pat. No. 5,405,755; U.S. Pat. No. 5,407,807; U.S. Patent Application Publication No. 2005-0171493; each herein incorporated by reference in their entireties). In some embodiments, the brush 130 has a handle 150 connected with the proximal end of a wire-body 160, and a bristle-section 170 connected to the distal end of the wire-body 180. In some embodiments, the bristle-section 170 contains a plurality of uniform or substantially uniform length bristles 190. In some embodiments, the bristle-section 170 contains a plurality of non-uniform (e.g., varied) length bristles 190. In some embodiments, the plurality bristles 190 protrude radially outward. In some embodiments, the plurality of bristles 190 protrude outward only at a specified degree (e.g., at a 90 degree angle). In some embodiments, the brush 130 is configured for positioning within the sheath 120, while the sheath 120 is attached with the catheter hub 110 via the sheath ring 140 such that the bristle section 170 is positioned within the catheter hub 110 (described in more detail below). In some embodiments, the brush 130 is configured for insertion through the catheter hub 110 and into a catheter for purposes of collecting a biological sample (described in more detail below). In some embodiments, the brush 130 is configured for re-insertion from a catheter and back through the catheter hub 110 and into the sheath 120 for purposes of storing a biological sample while preserving sterility (described in more detail below). The brush 130 is not limited to a particular length or width. In some embodiments, the size dimensions (e.g., length, width, weight) are such that it permits its insertion into a catheter of a desired length, and the collection of a biological sample (e.g., fibrin) from the catheter.

Still referring to FIG. 1, the catheter testing systems 100 of the present invention are not limited to a particular type or kind of sheath 120. The sheath 120 is not limited to a particular length or width. In some embodiments, the shape of the sheath 120 is tubular. In some embodiments, the length and width of the sheath 120 are such that it is able to store a brush 130 while attached with the catheter hub 110. In some embodiments, the sheath 120 has a sheath distal end 200, a sheath proximal end 210, and a sheath proximal end compartment 220. In some embodiments, the sheath proximal end 210 is closed, and the sheath distal end 200 is open. In some embodiments, the sheath distal end 200 is configured for attachment with the catheter hub 110 via the sheath ring 140 (described in more detail below). In some embodiments, as a biological sample is collected from a catheter and the brush 130 is withdrawn through the catheter hub 110 and into the sheath 120, the sheath 120 preserves sterility of the biological sample (described in more detail below). In some embodiments, the sheath proximal end compartment 220 has therein the brush handle 150 for purposes of preventing the brush handle 150 from advancement beyond the sheath 120 during use, and advancement of the brush 130 beyond a certain distance (described in more detail below). In some embodiments, the sheath proximal end compartment 220 is created with a sealant, or created with staggered sealants (as shown in FIG. 1). The sheath 120 is not limited to a particular material. In some embodiments, the material of the sheath 120 is polyethylene (e.g., 1 ml polyethylene). In some embodiments, the sheath 120 has double layer thereby providing additional durability. In some embodiments, the material of sheath 120 has high pliability and collapsibility such that as brush 130 is advanced or retreated through the catheter hub 110, the sheath 120 is able to compress to a higher amount thereby permitting advancement of the brush 130 further into a catheter.

Still referring to FIG. 1, the catheter testing systems 100 of the present invention are not limited to a particular type or kind of catheter hub 110. The catheter hub 110 is not limited to a particular size or shape. In some embodiments, the catheter hub 110 has a slip luer design, a luer lock design, or similar design. In some embodiments, the catheter hub 110 is configured to engage any type or kind or size of catheter. In some embodiments, the catheter hub 110 is configured to attach onto a catheter such that the brush 130 may be advanced through the catheter hub 110 and into the catheter for purposes of collecting a biological sample (described in more detail below).

Still referring to FIG. 1, in some embodiments, the catheter hub 110 has a catheter hub proximal end 230 and a catheter hub distal end 240. The catheter hub proximal end 230 is configured to receive the sheath 120 and sheath ring 140 around its outside edge such that the sheath 120 is securely attached with the catheter hub 110 (described in more detail). The catheter hub proximal end 230 is not limited to a particular opening size. The catheter hub distal end 240 is configured to removably engage any type, kind, shape or size of catheter such that a secure and sterile connection is made between the catheter and the catheter testing system 100. In some embodiments, the catheter hub 110 has a removable cap.

Still referring to FIG. 1, in some embodiments, both the catheter hub proximal end 230 and the catheter hub distal end 240 have openings such that the shape of the catheter hub 110 is similar to a tube. The catheter hub proximal end 230 is not limited to a particular opening size. In some embodiments, the size of the catheter hub proximal end 230 opening is such that a brush 130 may be passed into and out of the opening. The catheter hub distal end 240 is not limited to a particular opening size. In some embodiments, the size of the catheter hub distal end 240 opening is such that a brush may be passed into and out of the opening. In some embodiments, upon attachment of the sheath 120 and sheath ring 140 onto the outside portion of the catheter hub proximal end 230 and upon attachment of the catheter hub distal end 240 onto a catheter, a brush 130 positioned within the sheath 120 may be advanced through the catheter hub proximal end 230, through the catheter hub distal end 240, and into the catheter for purposes of collecting a biological sample from the interior of the catheter (described in more detail below).

Still referring to FIG. 1, the catheter testing systems 100 of the present invention are not limited to a particular type of sheath ring 140. The sheath ring 140 is not limited to a particular type of material. In some embodiments, the material of the sheath ring 140 can, for example, be metal, plastic, ceramic, wood, or mixture thereof. In some embodiments, the sheath ring 140 is configured to attach onto the catheter hub proximal end 230 for purposes of securing the sheath proximal end 210 with the catheter hub proximal end 230 (described in more detail below). The sheath ring 140 is not limited to a particular manner of attaching onto the catheter hub proximal end 230. In some embodiments, the sheath ring 140 slides securely onto the catheter hub proximal end 230. In some embodiments, the shape of the catheter hub proximal end 230 is such that the sheath ring 140 may snap onto the catheter hub proximal end 230. In some embodiments, upon attachment of the sheath ring 140 onto the catheter hub proximal end 230 thereby securing the sheath 120 onto the catheter hub proximal end 230, a sterile connection is made between the interior of the sheath 120 and the interior of the catheter hub 110.

The catheter testing systems of the present invention are not limited to particular uses. In some embodiments, the catheter testing systems may be used to collect a biological sample from the interior of a catheter. In some embodiments, a biological sample collected with the catheter testing systems of the present invention may be tested for any number of purposes (e.g., infection, blood type, debris, etc.) with any type of biological testing. The catheter testing systems are not limited to a particular type of manner of use. In some embodiments, the catheter testing systems may be used in a manner such that the cap (if present) is removed from the catheter hub distal end in a sterile manner, the catheter hub distal end is attached onto the proximal opening of a catheter (e.g., a catheter positioned within a subject), the brush is advanced through the catheter hub and into the catheter such that the brush handle does not advance beyond the sheath due to the sheath proximal end compartment, the brush bristles contact the interior walls of the catheter thereby collecting a biological sample from the catheter, the brush is retracted through the catheter hub and into the sheath, the cap (if present) is replaced onto the catheter hub distal end in a sterile manner, the catheter testing system delivered to a testing facility (e.g., a hospital laboratory), the biological sample removed from the catheter testing system, and the biological sample tested.

In certain embodiments, the devices have a catheter hub distal end secured with a catheter, with the sheath secured onto the outside of the catheter hub proximal end with a sheath ring, thereby securing sterility within the sheath, catheter hub, and catheter. In addition, the brush is positioned within sheath such that the brush handle is positioned at the proximal end of the sheath (e.g., within the sheath proximal end compartment so as to prevent advancement of the brush beyond the sheath and/or advancement of the brush beyond a certain distance within the catheter).

In certain embodiments, the devices have a catheter hub distal end is secured with a catheter. The sheath is secured onto the outside of the catheter hub proximal end with a sheath ring, thereby securing sterility within the sheath, catheter hub, and catheter.

In certain embodiments, the devices have a catheter hub distal end is secured with a catheter, with the sheath secured onto the outside of the catheter hub proximal end with a sheath ring, thereby securing sterility within the sheath, catheter hub, and catheter. In some embodiments, the brush is advanced through the catheter hub and into the catheter thereby compressing the sheath thereby displaying the high compressibility of the sheath thereby permitting further advancement of the brush into the catheter. In addition, as the brush is advanced through the catheter hub and into the catheter, the sheath remains attached onto the catheter hub due to its attachment with the sheath ring.

The catheter testing systems provide improvements over alternative testing methods. For example, the catheter testing systems provide improved sterility due to the attachment of the sheath onto the catheter hub with the sheath ring. One problem with alternative testing methods is the inability to reliably retain a sterile environment due to the slippage of the a sheath while collecting and storing a biological sample. The catheter testing systems of the present invention overcome this problem through securing of the sheath onto the catheter hub in a rigid manner with the sheath ring. As such, the catheter testing systems of the present invention provide a reliable manner for collecting biological sample from a catheter that was previously unavailable.

An additional improvement provided by the catheter testing systems of the present invention over previous methods is the securing of the of the brush handle within a sheath proximal end compartment. One problem with previous testing methods was the undesired advancement of the entire brush beyond the sheath. Such an occurrence rendered recapturing of the brush difficult, and often required the loss of sterility. Moreover, such an occurrence could lead to the advancement of the brush beyond a desired point (e.g., beyond the end of the catheter and into living body tissue). The catheter testing systems of the present invention overcome this problem by securing the brush handle within a sheath based compartment (e.g., the sheath proximal end compartment). In use, the sheath based compartment securing the brush handle prevents the brush from advancing beyond the sheath, and prevents the brush from advancing beyond a certain distance within the catheter.

In certain embodiments, the present invention provides methods for collecting a biological sample within a catheter positioned within a subject. In some embodiments, the method comprises securing a catheter testing system with a catheter positioned on a subject, the advancement of a brush through the catheter hub and into the catheter such that a biological sample is collected, and the removal of the brush back into the sheath of the catheter testing system. In some embodiments, the sheath ring prevents the disattachment or loosening of the sheath from the catheter hub thereby securing sterility. In some embodiments, the brush is prevented from advancing beyond the end of the sheath due to the securing of the brush handle within a sheath compartment (e.g., the sheath proximal end compartment). The methods are not limited to a particular type or form of testing of the collected biological sample.

In certain embodiments, the present invention provides kits comprising the catheter testing systems of the present invention. In some embodiments, the present invention provides kits comprising catheter testing systems and additional agents. Additional agents include, but are not limited to, an instruction sheet, medical gloves (e.g., Nitril Powder Free Gloves), a catheter (e.g., a 20 cm. 7-7.5-8 fr. Central Venous Catheter), facemasks (e.g., Earloop Procedure Face Masks), alcohol swabsticks, vacutainer tubes, an overwrap drape, a medical procedure drape, and a specimen transport bag.

We claim:

1. A device for collecting biological sample from an interior of a catheter, comprising
  a catheter hub, wherein said catheter hub is hollow and has therein a catheter hub proximal opening and a catheter hub distal opening, wherein said catheter hub distal opening is configured to engage a catheter opening, wherein said catheter hub proximal opening has therein a catheter hub proximal opening interior and a catheter hub proximal opening exterior, wherein said catheter hub distal opening has therein a catheter hub distal opening interior and a catheter hub distal opening exterior;
  a sheath, wherein said sheath is tubular in shape and has therein an open sheath distal end, a sheath proximal end compartment, and a closed sheath proximal end, wherein said open sheath distal end is securely positioned along the exterior of said catheter hub proximal opening, wherein said sheath proximal end compartment comprises said closed sheath proximal end and a sheath proximal end compartment distal end, wherein said sheath proximal end compartment distal end is partially sealed with said sheath thereby creating a segregated region within said sheath; and
  a brush, wherein said brush comprises a sample collection section, an extended body, a bristle section, and a brush handle, wherein said brush is positioned within said sheath such that said handle is positioned within said sheath proximal end compartment and said bristle section is positioned near said open sheath distal end such that said sample collection section may be advanced or withdrawn through said catheter hub, wherein as said brush is advanced or withdrawn through said catheter hub said partially sealed sheath proximal end compartment distal end prevents said brush handle from exiting said sheath proximal end compartment.

2. The device of claim 1, wherein said brush and said catheter have a length, wherein the length of said brush is less than the length of said catheter.

3. The device of claim 1, wherein said catheter hub is a slip luer.

4. The device of claim 1, wherein said positioning of said sheath distal end and said catheter hub proximal end preserves a sterile field within said sheath and said catheter hub.

5. The device of claim 1, wherein said sample collection section comprises bristles.

6. The device of claim 5, wherein said bristles are of uniform length.

7. The device of claim 5, wherein said bristles have varied length.

8. The device of claim 1, wherein said sheath has a material, wherein the material of said sheath is polyethylene.

9. A method of collecting a biological sample from the interior of a catheter, comprising:
   providing a subject having a catheter and the catheter testing device of claim 1;
   attaching said catheter hub distal end onto said catheter;
   advancing said brush through said catheter hub and into said catheter,
   collecting a biological sample from the interior of said catheter with said sample collection section of said brush, and
   withdrawing said brush from said catheter and into said sheath.

10. The method of claim 9, wherein said advancing, collecting and withdrawing is completed within a sterile field.

11. The method of claim 9, wherein said collected biological sample is tested for infection.

12. A kit for collecting a biological sample from the interior of a catheter, comprising the catheter testing device of claim 1.

13. The kit of claim 12, further comprising an additional agent selected from the group consisting of an instruction sheet, medical gloves, a catheter, a facemask, alcohol swabsticks, vacutainer tubes, an overwrap drape, a medical procedure drape, and a specimen transport bag.

14. The device of claim 1, wherein said device further comprises a sheath ring, wherein said sheath ring is hollow and ring shaped, wherein said sheath ring is positioned on the exterior of said open sheath distal end and catheter hub proximal end so as to secure said open sheath distal end on the exterior of said catheter hub proximal end.

15. The device of claim 5, wherein said bristle section of said brush is designed to collect biological sample from the interior of a catheter.

16. The method of claim 9, wherein said brush is advanced through said catheter hub and into said catheter such that said brush does not advance beyond terminus of said catheter.

17. The device of claim 1, wherein said polyethylene is 1 ml polyethylene.

18. The device of claim 1, wherein said sheath is double layer polyethylene.

19. The device of claim 1, wherein said sheath has pliability and collapsibility.

20. The device of claim 1, where said brush and said catheter have a length, wherein the length of said brush is more than the length of said catheter.

21. The method of claim 9, wherein said brush is advanced through said catheter hub and into said catheter such that said brush advances beyond terminus of said catheter.

* * * * *